(12) United States Patent
Burk et al.

(10) Patent No.: US 6,410,591 B1
(45) Date of Patent: Jun. 25, 2002

(54) 3,7 OR 3 AND 7 THIA OR OXA PROSTANOIC ACID DERIVATIVES AS AGENTS FOR LOWERING INTRAOCULAR PRESSURE

(75) Inventors: Robert M. Burk; Mark Holoboski; Mari F. Posner, all of Laguna Niguel, CA (US)

(73) Assignee: Allergan Sales, Inc., Irvine, CA (US)

( * ) Notice: Subject to any disclaimer, the term of this patent is extended or adjusted under 35 U.S.C. 154(b) by 0 days.

(21) Appl. No.: 09/851,296

(22) Filed: May 8, 2001

(51) Int. Cl.[7] ............... A01N 37/08; C07C 405/00; C07C 177/00
(52) U.S. Cl. ............... 514/530; 514/573; 514/613; 514/608; 548/252; 548/253; 560/121; 562/503
(58) Field of Search ................ 514/530, 573, 514/613, 608; 548/253, 252; 560/121, 503

(56) References Cited

U.S. PATENT DOCUMENTS

| | | |
|---|---|---|
| 5,892,099 A | 4/1999 | Maruyama et al. |
| 6,043,275 A | 3/2000 | Maruyama et al. |

FOREIGN PATENT DOCUMENTS

| | | |
|---|---|---|
| EP | 0 855 389 | 7/1998 |
| EP | 0 985 663 | 3/2000 |
| JP | 10-265454 | 10/1998 |
| JP | 2000-1472 | 1/2000 |

*Primary Examiner*—Paul J. Killos
(74) *Attorney, Agent, or Firm*—Robert J. Baran; Martin A. Voet; Carlos A. Fisher

(57) ABSTRACT

The present invention provides a method of treating ocular hypertension or glaucoma which comprises administering to an animal having ocular hypertension or glaucoma a therapeutically effective amount of a 3, 7 or 3 and 7 thia or oxa prostanoic acid derivative.

15 Claims, 3 Drawing Sheets

3,7 OR 3 AND 7 THIA OR OXA PROSTANOIC ACID DERIVATIVES AS AGENTS FOR LOWERING INTRAOCULAR PRESSURE

FIELD OF THE INVENTION

The present invention relates to 3, 7 or 3 and 7 thia or oxa prostanoic acid derivatives as potent ocular hypotensives that are particularly suited for the management of glaucoma.

BACKGROUND OF THE INVENTION

Description of Related Art

Ocular hypotensive agents are useful in the treatment of a number of various ocular hypertensive conditions, such as post-surgical and post-laser trabeculectomy ocular hypertensive episodes, glaucoma, and as presurgical adjuncts.

Glaucoma is a disease of the eye characterized by increased intraocular pressure. On the basis of its etiology, glaucoma has been classified as primary or secondary. For example, primary glaucoma in adults (congenital glaucoma) may be either open-angle or acute or chronic angle-closure. Secondary glaucoma results from pre-existing ocular diseases such as uveitis, intraocular tumor or an enlarged cataract.

The underlying causes of primary glaucoma are not yet known. The increased intraocular tension is due to the obstruction of aqueous humor outflow. In chronic open-angle glaucoma, the anterior chamber and its anatomic structures appear normal, but drainage of the aqueous humor is impeded. In acute or chronic angle-closure glaucoma, the anterior chamber is shallow, the filtration angle is narrowed, and the iris may obstruct the trabecular meshwork at the entrance of the canal of Schlemm. Dilation of the pupil may push the root of the iris forward against the angle, and may produce pupilary block and thus precipitate an acute attack. Eyes with narrow anterior chamber angles are predisposed to acute angle-closure glaucoma attacks of various degrees of severity.

Secondary glaucoma is caused by any interference with the flow of aqueous humor from the posterior chamber into the anterior chamber and subsequently, into the canal of Schlemm. Inflammatory disease of the anterior segment may prevent aqueous escape by causing complete posterior synechia in iris bombe, and may plug the drainage channel with exudates. Other common causes are intraocular tumors, enlarged cataracts, central retinal vein occlusion, trauma to the eye, operative procedures and intraocular hemorrhage.

Considering all types together, glaucoma occurs in about 2% of all persons over the age of 40 and may be asymptotic for years before progressing to rapid loss of vision. In cases where surgery is not indicated, topical b-adrenoreceptor antagonists have traditionally been the drugs of choice for treating glaucoma.

Certain eicosanoids and their derivatives have been reported to possess ocular hypotensive activity, and have been recommended for use in glaucoma management. Eicosanoids and derivatives include numerous biologically important compounds such as prostaglandins and their derivatives. Prostaglandins can be described as derivatives of prostanoic acid which have the following structural formula:

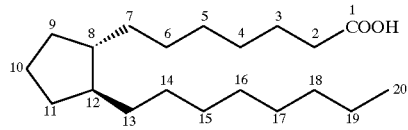

Various types of prostaglandins are known, depending on the structure and substituents carried on the alicyclic ring of the prostanoic acid skeleton. Further classification is based on the number of unsaturated bonds in the side chain indicated by numerical subscripts after the generic type of prostaglandin [e.g. prostaglandin $E_1$ ($PGE_1$), prostaglandin $E_2$ ($PGE_2$)], and on the configuration of the substituents on the alicyclic ring indicated by α or β [e.g. prostaglandin $F_{2\alpha}$ ($PGF_{2\beta}$)].

Prostaglandins were earlier regarded as potent ocular hypertensives, however, evidence accumulated in the last decade shows that some prostaglandins are highly effective ocular hypotensive agents, and are ideally suited for the long-term medical management of glaucoma (see, for example, Bito, L. Z. *Biological Protection with Prostaglandins*, Cohen, M. M., ed., Boca Raton, Fla., CRC Press Inc., 1985, pp. 231–252; and Bito, L. Z., *Applied Pharmacology in the Medical Treatment of Glaucomas* Drance, S. M. and Neufeld, A. H. eds., New York, Grune & Stratton, 1984, pp. 477–505. Such prostaglandins include $PGF_{2\alpha}$, $PGF_{1\alpha}$, $PGE_2$, and certain lipid-soluble esters, such as $C_1$ to $C_2$ alkyl esters, e.g. 1-isopropyl ester, of such compounds.

Although the precise mechanism is not yet known experimental results indicate that the prostaglandin-induced reduction in intraocular pressure results from increased uveoscleral outflow [Nilsson et.al., *Invest. Ophthalmol. Vis. Sci.* (suppl), 284 (1987)].

The isopropyl ester of $PGF_{2\alpha}$ has been shown to have significantly greater hypotensive potency than the parent compound, presumably as a result of its more effective penetration through the cornea. In 1987, this compound was described as "the most potent ocular hypotensive agent ever reported" [see, for example, Bito, L. Z., *Arch. Ophthalmol.* 105, 1036 (1987), and Siebold et.al., *Prodrug* 5 3 (1989)].

Whereas prostaglandins appear to be devoid of significant intraocular side effects, ocular surface (conjunctival) hyperemia and foreign-body sensation have been consistently associated with the topical ocular use of such compounds, in particular $PGF_{2\alpha}$ and its prodrugs, e.g., its 1-isopropyl ester, in humans. The clinical potentials of prostaglandins in the management of conditions associated with increased ocular pressure, e.g. glaucoma are greatly limited by these side effects.

In a series of co-pending United States patent applications assigned to Allergan, Inc. prostaglandin esters with increased ocular hypotensive activity accompanied with no or substantially reduced side-effects are disclosed. The co-pending U.S. Ser. No. 596,430 (filed Oct. 10, 1990, now U.S. Pat. No. 5,446,041), relates to certain 11-acyl-prostaglandins, such as 11-pivaloyl, 11-acetyl, 11-isobutyryl, 11-valeryl, and 11-isovaleryl $PGF_{2\alpha}$. Intraocular pressure reducing 15-acyl prostaglandins are disclosed in the co-pending application U.S. Ser. No. 175, 476 (filed Dec. 29, 1993). Similarly, 11,15- 9,15 and 9,11-diesters of prostaglandins, for example 11,15-dipivaloyl $PGF_{2\alpha}$ are known to have ocular hypotensive activity. See the co-pending patent applications U.S. Ser. No. 385,645 (filed Jul. 7, 1989, now U.S. Pat. No. 4,994,274), U.S. Ser.

No. 584,370 (filed Sep. 18, 1990, now U.S. Pat. No. 5,028, 624) and U.S. Ser. No. 585,284 (filed Sep. 18, 1990, now U.S. Pat. No. 5,034,413). The disclosures of all of these patent applications are hereby expressly incorporated by reference.

Certain 3, 7 dithiaprostanoic acid derivatives are disclosed in the following patents which are hereby incorporated by reference in their entirety. U.S. Pat. No. 6,043, 275 to Maruyama et al; U.S. Pat. No. 5,892,099 to Maruyama et al; EP 0 855 389; EP 0 985 663; Japanese Patent Publication 2000-1472 and Japanese Patent Publication 10-265454.

SUMMARY OF THE INVENTION

The present invention concerns a method of treating ocular hypertension which comprises administering to a mammal having ocular hypertension a therapeutically effective amount of a compound of formula I

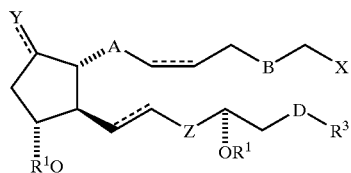

wherein hatched lines represent the α configuration, a triangle represents the β configuration and a dotted line represents the presence or absence of a double bond;

A and B are independently selected from the group consisting of O, S and $CH_2$, provided that at least one of A or B is S;

D represents a covalent bond or $CH_2$, O, S or NH;

X is $CO_2R$, $CONR_2$, $CH_2OR$, $P(O)(OR)_2$, $CONRSO_2R$, $SONR_2$ or

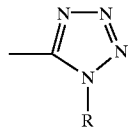

Y is O, OH, $OCOR^2$, halogen or cyano;

Z is $CH_2$ or a covalent bond;

R is H or $R^2$;

$R^1$ is H, $R^2$, phenyl, or $COR^2$;

$R^2$ is $C_1$–$C_5$ lower alkyl and $R^3$ is $C_1$–$C_5$ n-alkyl, $C_3$–$C_7$ cycloalkyl, phenyl, furanyl, thienyl, or substituted derivatives thereof, wherein the substituents maybe selected from the group consisting of $C_1$–$C_5$ alkyl, halogen, $CF_3$, CN, $NO_2$, $NR_2$, $CO_2R$ and OR.

In a still further aspect, the present invention relates to a pharmaceutical product, comprising a container adapted to dispense its contents in a metered form; and an ophthalmic solution therein, as hereinabove defined.

Finally, certain of the compounds represented by the above formula, disclosed below and utilized in the method of the present invention are novel and unobvious.

BRIEF DESCRIPTION OF THE DRAWING FIGURES

DETAILED DESCRIPTION OF THE INVENTION

Figure 1:
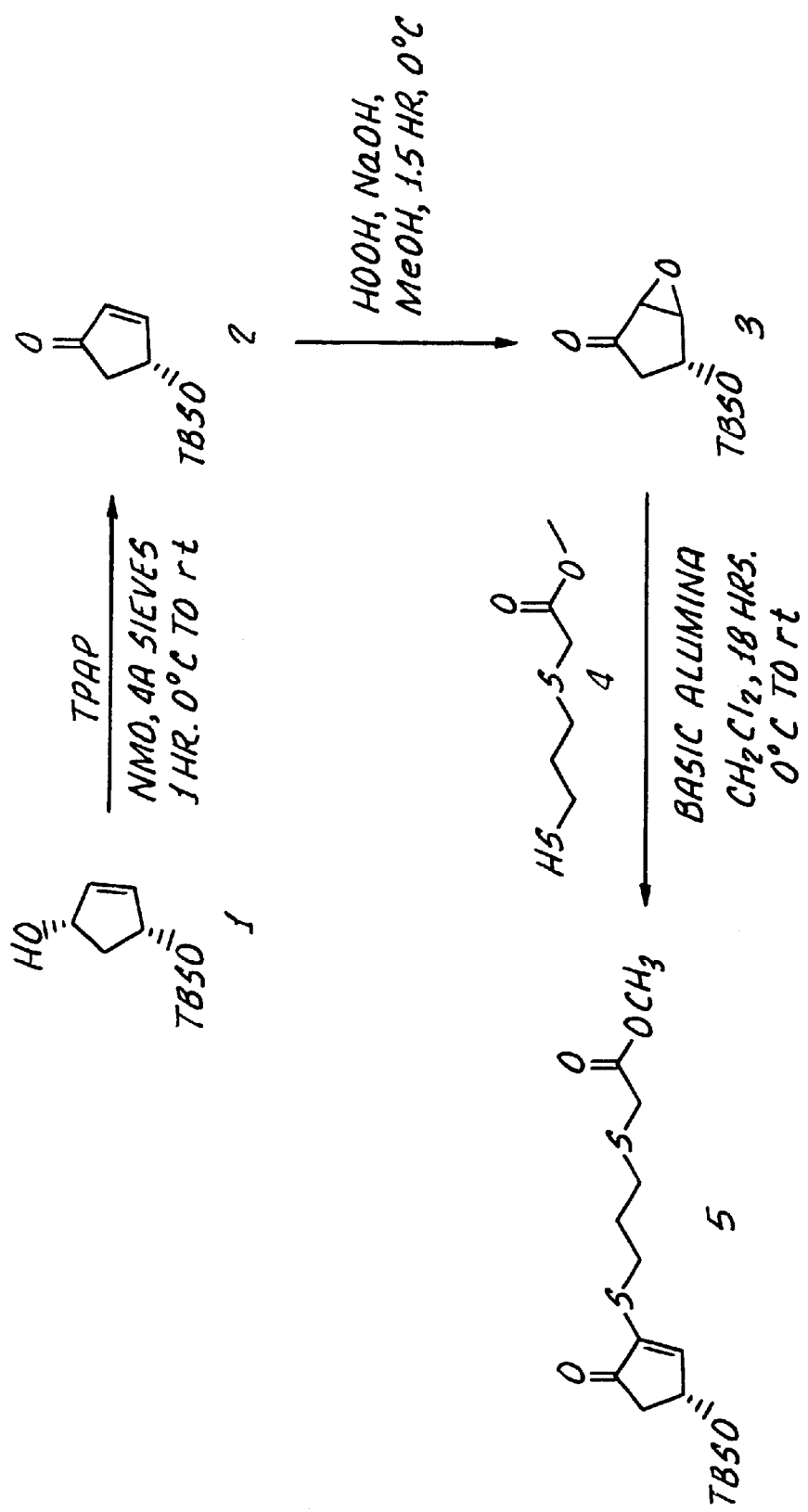
FIG. 1 is a schematic of the chemical synthesis of a certain intermediate useful in the chemical synthesis of certain of the compounds of the invention.

The present invention relates to the use of 3, 7 or 3 and 7 thia or oxa prostanoic acid derivatives as ocular hypotensives. The compounds used in accordance with the present invention are encompassed by the following structural formula I:

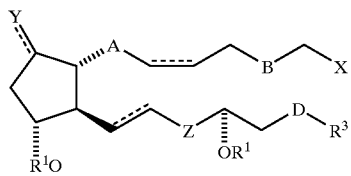

A preferred group of the compounds of the present invention includes compounds that have the following structural formula II:

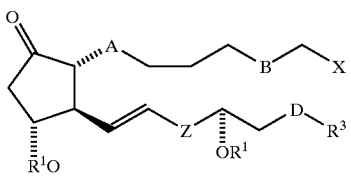

Another preferred group includes compounds having the formula III:

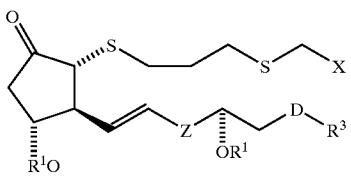

In the above formulae, the substituents and symbols are as hereinabove defined.

In the above formulae:

Preferably A and B are both S.

Preferably D represents a covalent bond or is $CH_2$.

Preferably R is H.

Preferably $R^1$ is H.

Preferably when D represents a covalent bond, $R^3$ is n-butyl or 1-propyl cyclobutyl.

Preferably Y=O.

Preferably X is $CO_2R$ and more preferably R is selected from the group consisting of H, methyl and i-propyl.

The above compounds of the present invention may be prepared by methods that are known in the art or according to the working examples below. The compounds, below, are especially preferred representative, of the compounds of the present invention.

{3-[(1R,2S,3R)-3-Hydroxy-2-((S)-(E)-3-hydroxyoct-1-enyl)-5-oxocyclopentyl-sulfanyl]propylsulfanyl}acetic acid methyl ester.

{3-[(1R,2S,3R)-3-Hydroxy-2-((S)-(E)-3-hydroxyoct-1-enyl)-5-oxocyclopentyl-sulfanyl]propylsulfanyl}acetic acid.

{3-[(1R,2S,3R)-3-Hydroxy-2-((S)-(E)-3-hydroxyoct-1-enyl)-5-oxocyclopentyl-sulfanyl]propylsulfanyl}acetic acid isopropyl ester.

(3-{(1R,2S,3R)-3-Hydroxy-2-[(E)-4-hydroxy-4-(1-propylcyclobutyl)but-1-enyl]-5-oxocyclopentylsulfanyl}propylsulfanyl)acetic acid methyl ester.

(3-{(1R,2S,3R)-3-Hydroxy-2-[(E)-4-hydroxy-4-(1-propylcyclobutyl)but-1-enyl]-5-oxocyclopentylsulfanyl}propylsulfanyl)acetic acid.

Pharmaceutical compositions may be prepared by combining a therapeutically effective amount of at least one compound according to the present invention, or a pharmaceutically acceptable acid addition salt thereof, as an active ingredient, with conventional ophthalmically acceptable pharmaceutical excipients, and by preparation of unit dosage forms suitable for topical ocular use. The therapeutically efficient amount typically is between about 0.0001 and about 5% (w/v), preferably about 0.001 to about 1.0% (w/v) in liquid formulations.

For ophthalmic application, preferably solutions are prepared using a physiological saline solution as a major vehicle. The pH of such ophthalmic solutions should preferably be maintained between 6.5 and 7.2 with an appropriate buffer system. The formulations may also contain conventional, pharmaceutically acceptable preservatives, stabilizers and surfactants.

Preferred preservatives that may be used in the pharmaceutical compositions of the present invention include, but are not limited to, benzalkonium chloride, chlorobutanol, thimerosal, phenylmercuric acetate and phenylmercuric nitrate. A preferred surfactant is, for example, Tween 80. Likewise, various preferred vehicles may be used in the ophthalmic preparations of the present invention. These vehicles include, but are not limited to, polyvinyl alcohol, povidone, hydroxypropyl methyl cellulose, poloxamers, carboxymethyl cellulose, hydroxyethyl cellulose and purified water.

Tonicity adjustors may be added as needed or convenient. They include, but are not limited to, salts, particularly sodium chloride, potassium chloride, mannitol and glycerin, or any other suitable ophthalmically acceptable tonicity adjustor.

Various buffers and means for adjusting pH may be used so long as the resulting preparation is ophthalmically acceptable. Accordingly, buffers include acetate buffers, citrate buffers, phosphate buffers and borate buffers. Acids or bases may be used to adjust the pH of these formulations as needed.

In a similar vein, an ophthalmically acceptable antioxidant for use in the present invention includes, but is not limited to, sodium metabisulfite, sodium thiosulfate, acetylcysteine, butylated hydroxyanisole and butylated hydroxytoluene.

Other excipient components which may be included in the ophthalmic preparations are chelating agents. The preferred chelating agent is edentate disodium, although other chelating agents may also be used in place or in conjunction with it.

The ingredients are usually used in the following amounts:

| Ingredient | Amount (% w/v) |
| --- | --- |
| active ingredient | about 0.001–5 |
| preservative | 0–0.10 |
| vehicle | 0–40 |
| tonicity adjustor | 1–10 |
| buffer | 0.01–10 |
| pH adjustor | q.s. pH 4.5–7.5 |
| antioxidant | as needed |
| surfactant | as needed |
| purified water | as needed to make 100% |

The actual dose of the active compounds of the present invention depends on the specific compound, and on the condition to be treated; the selection of the appropriate dose is well within the knowledge of the skilled artisan.

The ophthalmic formulations of the present invention are conveniently packaged in forms suitable for metered application, such as in containers equipped with a dropper, to facilitate the application to the eye. Containers suitable for dropwise application are usually made of suitable inert, non-toxic plastic material, and generally contain between about 0.5 and about 15 ml solution.

Figure 2:
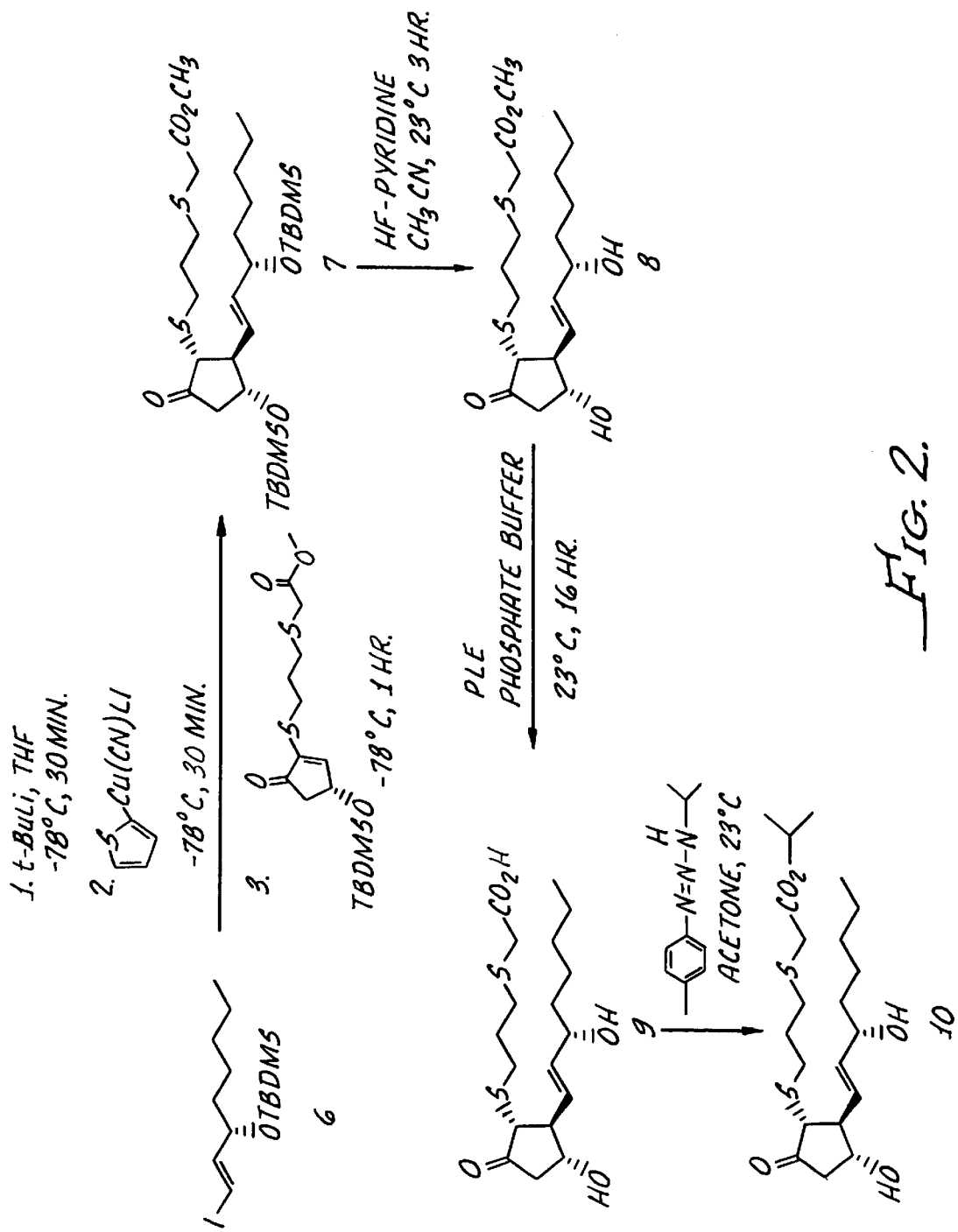
FIG. 2 is a schematic of the chemical synthesis of certain compounds of the invention as disclosed in Examples 5 through 7.
Figure 3:
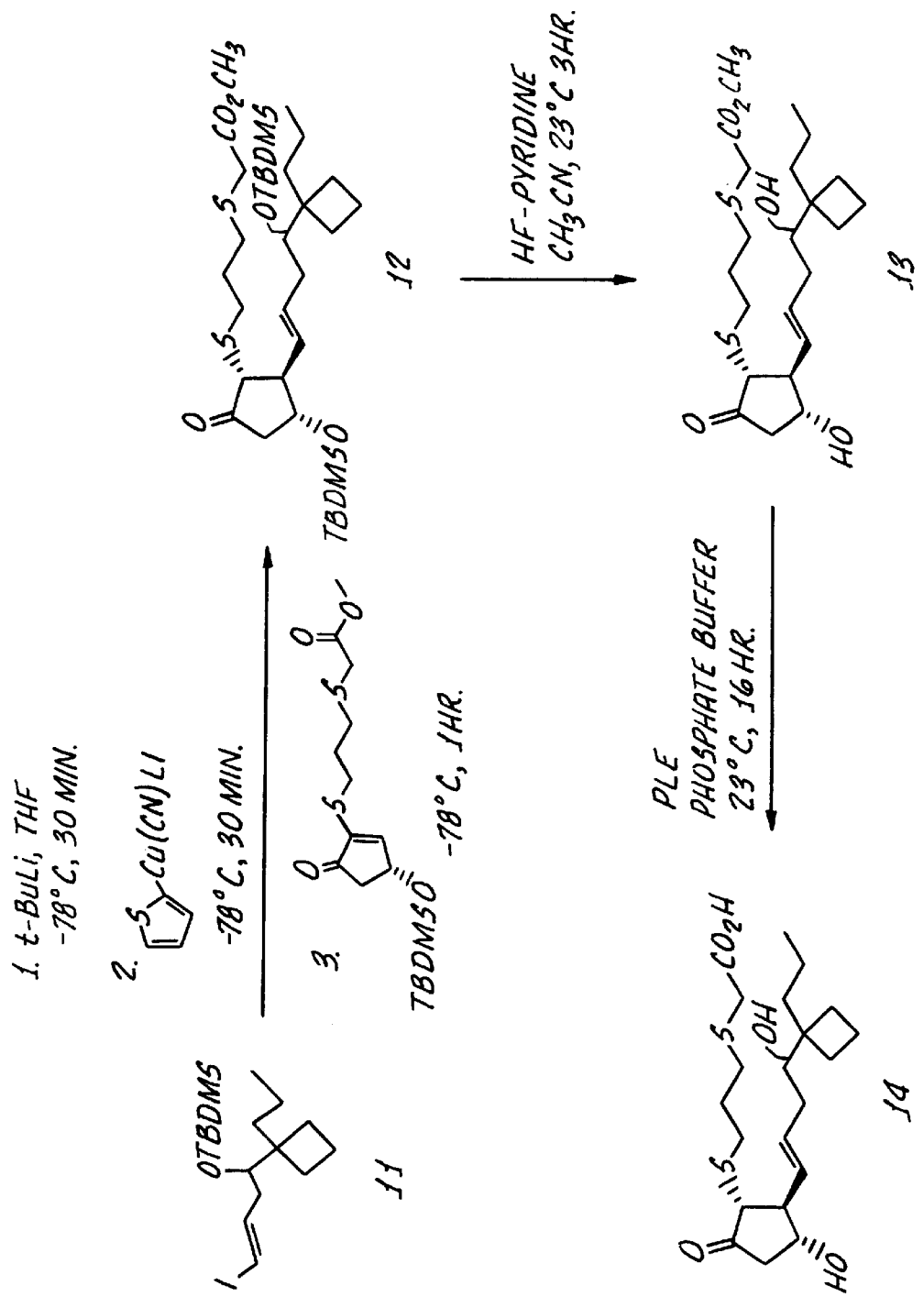
FIG. 3 is a schematic of the chemical synthesis of certain compounds of the invention as disclosed in Examples 9 and 10.

The invention is further illustrated by the following non-limiting Examples, which are summarized in the reaction schemes of FIGS. 1 through 3 wherein the compounds are identified by the same designator in both the Examples and the Figures.

EXAMPLE 1

(R)-4-(tert-Butyldimethylsilanyloxy)cyclopent-2-enone (2)

Tetrapropylammonium perruthenate (9.4 mg, 0.027 mmol) was added to a mixture of (1S, 4R)-4-(tert-butyldimethylsilanyloxy)cyclopent-2-enol prepared, according to Tetrahedron Letters, Vol. 37, No. 18, 1996, pp. 3083–6, (118.6 mg, 0.54 mmol), 4-methylmorpholine N-oxide (94.9 mg, 0.81 mmol) and crushed 4Å sieves (270 mg) in $CH_2Cl_2$ (10 mL). The mixture was stirred for 30 min and was passed through a plug of silica gel with $CH_2Cl_2$. The filtrate was concentrated in vacuo to give 100 mg (86%) of the above titled compound.

EXAMPLE 2

(R)-4-(tert-Butyldimethylsilanyloxy)-6-oxabicyclo[3.1.0]hexan-2-one (3)

Hydrogen peroxide (4.5 mL, 46.3 mmol, 30% by wt.) and 1N NaOH (46 μL, 0.046 mmol) were added to a solution of enone 2 (2.5 g, 11.5 mmol) in MeOH (30 mL) at 0° C. After stirring 1.5 h at 0° C. the mixture was concentrated in vacuo, washed with saturated aqueous $NH_4Cl$ and extracted with $CH_2Cl_2$ (3×). The combined organics were washed with brine, dried ($Na_2SO_4$), filtered and concentrated in vacuo to afford the above titled compound.

EXAMPLE 3

({3-[(R)-3-(tert-Butyldimethylsilanyloxy)-5-oxocyclopent-1-enylsulfanyl]propyl-sulfanyl}acetic acid methyl ester (5)

The epoxide 3 prepared above was diluted with $CH_2Cl_2$ (30 mL), (3-mercaptopropylsulfanyl) acetic acid methyl ester 4 (1.93 g, 10.7 mmol), prepared according to Chem.

Pharm. Bull. 28 (2), 1980, 558–566, was added and the solution was cooled to 0° C. Basic alumina (11.9 g) was added and the reaction mixture was warmed to room temperature. After stirring for 18 h the mixture was filtered through celite and concentrated in vacuo. The residue was purified by flash column chromatography (silica gel, 6:1 hex/EtOAc) to yield 3.6 g (80%) of the above titled compound.

EXAMPLE 4

(3{(1R,2S,3R)-3-(tert-Butyldimethylsilanyloxy)-2-[(S)-(E)-3-(tert-butyldimethylsilanoxy)oct-1-enyl]-5-oxocyclopentylsulfanyl} propylsulfanyl)acetic acid methyl ester (7)

tert-Butyllithium (1.47 mL of a 1.7M solution in pentane, 2.5 mmol) was added dropwise to a solution of tert-butyl [(S)-1-((E)-2-iodovinyl) hexyloxy]dimethylsilane 6 (462.5 mg, 1.25 mmol) in $Et_2O$ (6.0 mL) at −78° C. After stirring for 30 min lithium 2-thienylcyanocuprate (6.0 mL of a 0.25M solution in THF, 1.5 mmol) was added and the reaction was stirred an additional 30 min at −78° C. A solution of enone 5 (430 mg, 1.1 mmol) in $Et_2O$ (1 mL) was added and stirring was continued for an additional 1 h. The reaction mixture was then quickly poured into saturated aqueous $NH_4Cl$ cooled to 0° C. The mixture was extracted with EtOAc and the organic portion was washed with brine, dried ($Na_2SO_4$), filtered and concentrated in vacuo. The residue was quickly purified by flash column chromatography (silica gel, 100% hexane followed by 8:1 hex/EtOAc) to afford 270 mg (39%) of the above titled compound.

EXAMPLE 5

{3-[(1R,2S,3R)-3-Hydroxy-2-((S)-(E)-3-hydroxyoct-1-enyl)-5-oxocyclopentyl-sulfanyl]propylsulfanyl}acetic acid methyl ester (8)

Hydrogen fluoride-pyridine (220 µL) was added to a solution of bis-TBDMS ether 7 (70 mg, 0.11 mmol) in $CH_3CN$ (2.0 mL) at 0° C. The reaction was warmed to room temperature, stirred 1 h, and recooled to 0° C. The reaction was quenched with saturated aqueous $NaHCO_3$ until gas evolution ceased. The mixture was extracted with $CH_2Cl_2$ (4×). The combined organics were washed with brine, dried ($Na_2SO_4$), filtered and concentrated in vacuo. Purification of the residue by flash column chromatography (silica gel, 100% $CH_2Cl_2$ followed by 30:1 $CH_2Cl_2$:MeOH) provided 40 mg (90%) of the above titled compound.

EXAMPLE 6

{3-[(1R,2S,3R)-3-Hydroxy-2-((S)-(E)-3-hydroxyoct-1-enyl)-5-oxocyclopentyl-sulfanyl]propylsulfanyl}acetic acid (9)

Methyl ester 8 (50 mg, 0.124 mmol) was dissolved in $CH_3CN$ (10 µL) and pH 7.2 phosphate buffer (3.0 mL) was added. The mixture was treated with PLE (400 µL, 1.34 µmol/µL) and stirred for 16 h at 23° C. The reaction mixture was extracted with EtOAc (3×). The combined organics were washed with brine, dried ($Na_2SO_4$), filtered and concentrated in vacuo. Purification of the residue by flash column chromatography (silica gel, 100% EtOAc) gave 5.3 mg (11%) of the above titled compound.

EXAMPLE 7

{3-[(1R,2S,3R)-3-Hydroxy-2-((S)-(E)-3-hydroxyoct-1-enyl)-5-oxocyclopentyl-sulfanyl]propylsulfanyl}acetic acid isopropyl ester (10)

Isopropyl-p-tolyltriazene (200 µL) was added dropwise to a solution of carboxylic acid 9 (10.5 mg, 0.026 mmol) in acetone (5.0 mL) at 23° C. After stirring for 1 h the reaction was quenched with 1N HCl and the solvent was removed in vacuo. The residue was extracted with $CH_2Cl_2$ (2×). The combined organics were dried ($Na_2SO_4$), filtered and concentrated in vacuo. Purification of the residue by flash column chromatography (silica gel, 4:1 hex/EtOAc) gave 4.3 mg (38%) of the above titled compound.

EXAMPLE 8

(3-{(1R,2S,3R)-3-(tert-Butyldimethylsilanyloxy)-2-[(E)4-(tert-butyldimethyl-silanoxy)4-(1-propylcyclobutyl)but-1-enyl]-5-oxocyclopentylsulfanyl}propyl-sulfanyl)acetic acid methyl ester (12)

According to the procedure described above in Example 4,150 mg (29%) of the above titled compound was prepared employing enone 5 (303 mg, 0.775 mmol) and tert-butyl-[(E)4-iodo-1-(1-propylcyclobutyl)but-3-enyloxy] dimethylsilane 11 (328 mg, 0.777 mmol).

EXAMPLE 9

(3-{(1R,2S,3R)-3-Hydroxy-2-[(E)4hydroxy4-(1-propylcyclobutyl)but-1-enyl]-5-oxocyclopentylsulfanyl}propylsulfanyl)acetic acid methyl ester (13)

According to the procedure described above in Example 5,7.9 mg (40%) of the above titled compound was prepared from enone 12 (30 mg, 0.045 mmol).

EXAMPLE 10

(3-{(1R,2S,3R)-3-Hydroxy-2-[(E)-4hydroxy-4-(1-propylcyclobutyl)but-1-enyl]-5-oxocyclopentylsulfanyl}propylsulfanyl)acetic acid (14)

According to the procedure described above in Example 6,4.1 mg (42%) of the above titled compound was prepared from ester 13 (10 mg, 0.023 mmol).

The effects of the compounds of this invention on intraocular pressure are also provided in the following tables. The compounds were prepared at the said concentrations in a vehicle comprising 0.1% polysorbate 80 and 10 mM TRIS base. Dogs were treated by administering 25 µl to the ocular surface, the contralateral eye received vehicle as a control. Intraocular pressure was measured by applanation pneumatonometry. Dog intraocular pressure was measured immediately before drug administration and at 6 hours thereafter.

Compounds 9 and 10 were examined and showed a pronounced ocular hypotensive effect in dogs and the glaucomatous cynomonlgus monkeys, respectively. Compound 9 at a dose of 0.1% w/v reduced the intraocular pressure (IOP) by 50% and at a dose of 0.01% w/v reduced the IOP by 45%.

Compound 10 at a dose of 0.01% w/v reduced the IOP in the glaucomatous cynomonlgus monkey.

The foregoing description details specific methods and compositions that can be employed to practice the present invention, and represents the best mode contemplated. However, it is apparent for one of ordinary skill in the art that further compounds with the desired pharmacological properties can be prepared in an analogous manner, and that the disclosed compounds can also be obtained from different starting compounds via different chemical reactions. Similarly, different pharmaceutical compositions may be prepared and used with substantially the same result. Thus, however detailed the foregoing may appear in text, it should not be construed as limiting the overall scope hereof; rather, the ambit of the present invention is to be governed only by the lawful construction of the appended claims.

What is claimed is:

1. A method of treating ocular hypertension or glaucoma which comprises administering to an animal having ocular hypertension or glaucoma a therapeutically effective amount of a compound represented by the general formula I;

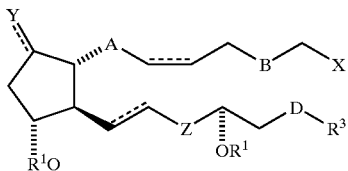

wherein hatched lines represent the α configuration, a triangle represents the β configuration and a dotted line represents the presence or absence of a double bond;

A and B are independently selected from the group consisting of O, S and $CH_2$, provided that at least one of A or B is S;

D represents a covalent bond or $CH_2$, O, S or NH;

X is $CO_2R$, $CONR_2$, $CH_2OR$, $P(O)(OR)_2$, $CONRSO_2R$, $SONR_2$ or

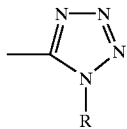

Y is O, OH, $OCOR^2$, halogen or cyano;

Z is $CH_2$ or a covalent bond;

R is H or $R^2$;

$R^1$ is H, $R^2$, phenyl, or $COR^2$;

$R^2$ is $C_1$–$C_5$ lower alkyl and $R_3$ is $C_1$–$C_5$ n-alkyl, $C_3$–$C_7$ cycloalkyl, phenyl, furanyl, thienyl, or substituted derivatives thereof, wherein the substituents maybe selected from the group consisting of $C_1$–$C_5$ alkyl, halogen, $CF_3$, CN, $NO_2$, $NR_2$, $CO_2R$ and OR.

2. The method according to claim 1 wherein said compound is represented by the general formula II;

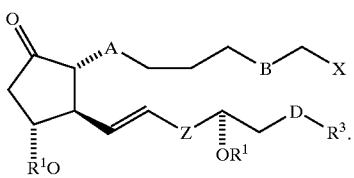

3. The method according to claim 2 wherein said compound is represented by the general formula III;

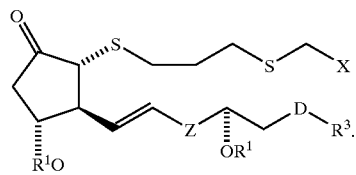

4. The method of claim 1 wherein A and B are both S.

5. The method of claim 1 wherein D represents a covalent bond or is $CH_2$.

6. The method of claim 1 wherein X is $CO_2R$.

7. The method of claim 6 wherein R is selected from the group consisting of H, methyl and i-propyl.

8. The method of claim 1 wherein R is H.

9. The method of claim 1 wherein $R_1$ is H.

10. The method of claim 1 wherein D represents a covalent bond.

11. The method of claim 10 wherein $R^3$ is n-butyl or 1-propylcyclobutyl.

12. The method of claim 1 wherein said compound is selected from the group consisting of {3-[(1R,2S,3R)-3-Hydroxy-2-((S)-(E)-3-hydroxyoct-1-enyl)-5-oxocyclopentylsulfanyl]propylsulfanyl}acetic acid methyl ester, {3-[(1R,2S,3R)-3-Hydroxy-2-((S)-(E)-3-hydroxyoct-1-enyl)-5-oxocyclopentylsulfanyl]propylsulfanyl}acetic acid, {3-[(1R,2S,3R)-3-Hydroxy-2-((S)-(E)-3-hydroxyoct-1-enyl)-5-oxocyclopentylsulfanyl]propylsulfanyl}acetic acid isopropyl ester, (3-{(1R,2S,3R)-3-Hydroxy-2-[(E)-4-hydroxy-4-(1-propylcyclobutyl)but-1-enyl]-5-oxocyclopentylsulfanyl}propylsulfanyl)acetic acid methyl ester, and (3-{(1R,2S,3R)-3-Hydroxy-2-[(E)-4-hydroxy-4-(1-propylcyclobutyl)but-1-enyl]-5-oxocyclopentylsulfanyl}propylsulfanyl)acetic acid.

13. An ophthalmic solution comprising a therapeutically effective amount of a compound represented by the general Formula 1

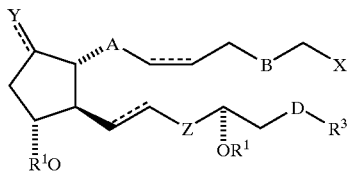

wherein hatched lines represent the α configuration, a triangle represents the β configuration and a dotted line represents the presence or absence of a double bond;

A and B are independently selected from the group consisting of O, S and $CH_2$ provided that at least one of A or B is S;

D represents a covalent bond or $CH_2$, O, S or NH;

X is $CO_2R$, $CONR_2$, $CH_2OR$, $P(O)(OR)_2$, $CONRSO_2R$ $SONR_2$ or

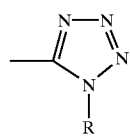

Y is O, OH, OCOR², halogen or group;
Z is CH₂ or a covalent bond;
R is H or R²;
R¹ is H, R², phenyl, or COR²;
R² is $C_1$–$C_5$ lower alkyl and R₃ is $C_1$–$C_5$ n-alkyl, $C_3$–$C_7$ cycloalkyl, phenyl, furanyl, thienyl, or substituted derivatives thereof, wherein the substituents maybe selected from the group consisting of $C_1$–$C_5$ alkyl, halogen, $CF_3$, CN, $NO_2$, $NR_2$, $CO_2R$ and OR in admixture with a non-toxic, ophthalmically acceptable liquid vehicle, packaged in a container suitable for metered application.

14. A pharmaceutical product, comprising a container adapted to dispense the contents of said container in metered form; and an ophthalmic solution according to claim 13 in said container.

15. A novel compound selected from the group consisting of

{3-[(1R,2S,3R)-3-Hydroxy-2-((S)-(E)-3-hydroxyoct-1-enyl)-5-oxocyclopentylsulfanyl]propylsulfanyl}acetic acid isopropyl ester (10).

(3-{(1R,2S,3R)-3-Hydroxy-2-[(E)-4-hydroxy-4-(1-propylcyclobutyl)but-1-enyl]-5-oxocyclopentylsulfanyl}propylsulfanyl)acetic acid methyl ester (13) and (3-{(1R,2S,3R)-3-Hydroxy-2-[(E)-4-hydroxy-4-(1-propylcyclobutyl)but-1-enyl]-5-oxocyclopentylsulfanyl}propylsulfanyl)acetic acid (14).

\* \* \* \* \*